(12) United States Patent
Sherwinter

(10) Patent No.: US 8,052,699 B1
(45) Date of Patent: Nov. 8, 2011

(54) VISCEROTOMY CLOSURE DEVICE AND METHOD OF USE

(75) Inventor: Danny Sherwinter, Brooklyn, NY (US)

(73) Assignee: Cook Medical Technologies LLC, Bloomington, IN (US)

( * ) Notice: Subject to any disclaimer, the term of this patent is extended or adjusted under 35 U.S.C. 154(b) by 775 days.

(21) Appl. No.: 12/152,329

(22) Filed: May 14, 2008

Related U.S. Application Data

(60) Provisional application No. 60/930,284, filed on May 15, 2007, provisional application No. 61/001,427, filed on Nov. 1, 2007.

(51) Int. Cl.
*A61B 17/115* (2006.01)
(52) U.S. Cl. ............... 606/153; 227/175.1; 606/216
(58) Field of Classification Search .... 227/175.1–182.1; 606/153, 151, 75, 219, 170, 180
See application file for complete search history.

(56) References Cited

U.S. PATENT DOCUMENTS

| | | | | |
|---|---|---|---|---|
| 5,395,030 | A * | 3/1995 | Kuramoto et al. | 227/179.1 |
| 5,919,232 | A * | 7/1999 | Chaffringeon et al. | 424/423 |
| 6,210,439 | B1 * | 4/2001 | Firmin et al. | 623/8 |
| 6,258,107 | B1 * | 7/2001 | Balazs et al. | 606/153 |
| 7,175,591 | B2 * | 2/2007 | Kaladelfos | 600/37 |
| 7,547,312 | B2 * | 6/2009 | Bauman et al. | 606/151 |
| 7,670,361 | B2 * | 3/2010 | Nesper et al. | 606/300 |
| 7,744,627 | B2 * | 6/2010 | Orban et al. | 606/215 |
| 7,823,592 | B2 * | 11/2010 | Bettuchi et al. | 128/898 |
| 7,845,536 | B2 * | 12/2010 | Viola et al. | 227/179.1 |
| 2003/0065402 | A1 * | 4/2003 | Anderson et al. | 623/23.66 |
| 2005/0245965 | A1 * | 11/2005 | Orban, III et al. | 606/214 |
| 2006/0085034 | A1 * | 4/2006 | Bettuchi | 606/219 |
| 2006/0135992 | A1 * | 6/2006 | Bettuchi et al. | 606/219 |
| 2006/0212050 | A1 * | 9/2006 | D'Agostino et al. | 606/151 |
| 2006/0271104 | A1 * | 11/2006 | Viola et al. | 606/214 |
| 2007/0175963 | A1 * | 8/2007 | Bilotti et al. | 227/179.1 |
| 2007/0203510 | A1 * | 8/2007 | Bettuchi | 606/153 |
| 2007/0246505 | A1 * | 10/2007 | Pace-Floridia et al. | 227/175.1 |
| 2008/0110959 | A1 * | 5/2008 | Orban et al. | 227/176.1 |
| 2008/0140115 | A1 * | 6/2008 | Stopek | 606/219 |

* cited by examiner

*Primary Examiner* — Julian Woo
*Assistant Examiner* — Christopher L Templeton
(74) *Attorney, Agent, or Firm* — Brinks Hofer Gilson & Lione

(57) ABSTRACT

Viscerotomy closure devices and methods of use close a hole in a bodily organ, such as one created during a natural orifice transgastric surgery procedure. A mesh with a hole in its center and an attached loop of suture having a Roeder knot is mounted on the protruding rod of an end-to-end anastomosis stapler between the anvil and the staple carrying member. The mesh covers the staple receiving slots. When rotated when in contact with tissue, an augur-shaped blade attached to the anvil's exterior self-feeds the tissue through a notch in the anvil's base into the space between the anvil and the staple carrying member. After the stapler is fired to staple the mesh to the tissue and create a viscerotomy, a knot pusher cinches the loop of suture and subsequently tightens the Roeder knot to maintain the cinch.

13 Claims, 6 Drawing Sheets

VISCEROTOMY CLOSURE DEVICE AND METHOD OF USE

CLAIM OF PRIORITY

This application claims priority and benefit of U.S. Provisional Application No. 60/930,284, filed on May 15, 2007, and further claims benefit of U.S. Provisional Application No. 61/001,427, filed on Nov. 1, 2007

BACKGROUND OF THE INVENTION

1. Field of the Invention

The present invention relates to a viscerotomy closure device and method of use for use in connection with closing a hole created during surgery. The viscerotomy closure device and method of use has particular utility in connection with closing a hole in a bodily' organ, such as one created during a natural orifice transgastric surgery procedure.

2. Description of the Prior Art

Viscerotomy closure devices and methods of use are desirable for closing a hole in a bodily organ, such as one created during a natural orifice transgastric surgery procedure. At the inception of transgastric surgery, a gastrotomy is created by placing a hole in a patient's stomach. The gastrotomy must be closed at the completion of the procedure. Conventional methods for creating and closing the gastrotomy are time consuming and increase the possibility of undesirable reopening of the gastrotomy.

The use of circular stapler tissue retention spring methods is known in the prior art. For example, U.S. Pat. No. 5,309,927 to Welch discloses a circular stapler tissue retention spring method. However, the Welch '927 patent does not have a suture entrapped by a circle of staples deployed by a circular stapler that acts as a purse string, and has further drawbacks of lacking an augur-shaped blade.

U.S. Pat. No. 7,182,239 to Myers discloses a segmented introducer device for a circular surgical stapler that is capable of fitting onto the center rods of circular stapling devices having different stapler head diameters. However, the Myers '239 patent does not have a suture entrapped by a circle of staples deployed by a circular stapler that acts as a purse string, and additionally does not have an augur-shaped blade.

Similarly, U.S. Pat. No. 5,197,648 to Gingold discloses a surgical stapling apparatus that joins hollow tubular organs. However, the Gingold '648 patent does not have a suture entrapped by a circle of staples deployed by a circular stapler that acts as a purse string, and cannot does not have an augur-shaped blade.

In addition, U.S. Pat. No. 5,261,920 to Main et al. discloses an anvil bushing for circular stapler that is for use with a surgical circular stapler. However, the Main et al. '920 patent does not have a suture entrapped by a circle of staples deployed by a circular stapler that acts as a purse string, and also does not have an augur-shaped blade.

Furthermore, U.S. Pat. No. 5,104,025 to Main et al. discloses an intraluminal anastomotic surgical stapler with detached anvil that is a surgical stapling mechanism. However, the Main et al. '025 patent does not have a suture entrapped by a circle of staples deployed by a circular stapler that acts as a purse string, and further lacks an augur-shaped blade.

United States Patent Application Publication Number 2007/0021759 to Griffith et al. discloses a flexible endoscopic anastomotic ring applier device that deploys an anastomotic ring device. However, the Griffith et al. 2007/0021759 patent application publication does not have a suture entrapped by a circle of staples deployed by a circular stapler that acts as a purse string, and has the additional deficiency of lacking an auger-shaped blade.

In addition, United States Patent Application Publication Number 2005/0228414 to Clanton et al. discloses an apparatus and method of use of a circular surgical stapler that removes a circumferential portion of a hollow body organ from a patient. However, the Clanton et al. 2005/0228414 patent application publication does not have a suture entrapped by a circle of staples deployed by a circular stapler that acts as a purse string, and also does not have an augur-shaped blade.

Furthermore, United States Patent Application Publication Number 2004/0217146 to Green discloses a surgical stapler apparatus and method that is a surgical stapler. However, the Green 2004/0217146 patent application publication does not have a suture entrapped by a circle of staples deployed by a circular stapler that acts as a purse string, and further lacks an auger-shaped blade.

U.S. Pat. No. 5,441,507 to Ahn discloses a laparoscopic or endoscopic anastomosis technique and associated instruments that performs an anastomosis. However, the Ahn '507 patent does not have a suture entrapped by a circle of staples deployed by a circular stapler that acts as a purse string, and has the additional deficiency of lacking an augur-shaped blade.

In addition, United States Patent Application Publication Number 2005/0038456 to Clanton et al. discloses an anastomosis device having a deployable section that includes a deployable section. However, the Clanton et al. 2005/0038456 patent application publication does not have a suture entrapped by a circle of staples deployed by a circular stapler that acts as a purse string, and also does not have a loop of suture.

Furthermore, United States Patent Application Publication Number 2007/0129739 to Green discloses an apparatus and method for performing a bypass procedure in a digestive system that performs a bypass procedure in a digestive system. However, the Green 2007/0129739 patent application publication does not have a suture entrapped by a circle of staples deployed by a circular stapler that acts as a purse string, and further lacks an auger-shaped blade.

United States Patent Application Publication Number 2007/0203510 to Alm discloses an annular disk for reduction of anastomotic tension and methods of using the same that forms an anastomosis between adjacent tissue sections. However, the Ahn 2007/0203510 patent application publication does not have a suture entrapped by a circle of staples deployed by a circular stapler that acts as a purse string, and has the additional deficiency of lacking an augur-shaped blade.

Furthermore, United States Patent Application Publication Number 2006/0136043 to Green discloses a filament-wound implementable devices that a self-expanding implantable medical device. However, the Green 2006/0136043 patent application publication does not have a suture entrapped by a circle of staples deployed by a circular stapler that acts as a purse string, and further lacks an auger-shaped blade.

European Patent Number EP1213989 to Ahn discloses a set of accessories for transitional operations and procedures for their use that remove a cylindrical or tubular section of mucosa from a rectal ampule. However, the Ahn EP1213989 patent does not have a suture entrapped by a circle of staples deployed by a circular stapler that acts as a purse string, and has the additional deficiency of lacking an augur-shaped blade.

In addition, U.S. Pat. No. 4,665,917 to Clanton et al. discloses a tissue gripper for use with intraluminal stapling device that holds tissue to be joined in the proper position with respect to the fasteners used to accomplish the fastening. However, the Clanton et al. '917 patent does not have a suture entrapped by a circle of staples deployed by a circular stapler that acts as a purse string, and also does not have a loop of suture.

Furthermore, U.S. Pat. No. 4,749,114 to Green discloses a purse string applicator and method of affixing a purse string that fixes a string about the periphery of an aperture with staples for use as a purse string. However, the Green '114 patent does not have a suture attached to a mesh entrapped by a circle of staples deployed by a circular stapler that acts as a purse string, and further lacks an auger-shaped blade.

Lastly, U.S. Pat. No. 5,571,117 to Ahn discloses a method of endoscopic stapling and suturing and instrument therefor that removably positions a suture in front of and in registry with the staple discharge opening such that a staple discharge therefrom will affix the suture to a target tissue. However, the Ahn '117 patent application publication does not have a suture attached to a mesh entrapped by a circle of staples deployed by a circular stapler that acts as a purse string, and has the additional deficiency of lacking an augur-shaped blade.

While the above-described devices fulfill their respective, particular objectives and requirements, the aforementioned patents do not describe a viscerotomy closure device and method of use that allows closing a hole in a bodily organ, such as one created during a natural orifice transgastric surgery procedure.

Therefore, a need exists for a new and improved viscerotomy closure device and method of use that can be used for closing a hole in a bodily organ, such as one created during a natural orifice transgastric surgery procedure. In this regard, the present invention substantially fulfills this need. In this respect, the viscerotomy closure device and method of use according to the present invention substantially departs from the conventional concepts and designs of the prior art, and in doing so provides an apparatus primarily developed for the purpose of closing a hole in a bodily organ, such as one created during a natural orifice transgastric surgery procedure.

SUMMARY OF THE INVENTION

In view of the foregoing disadvantages inherent in the known types of circular stapler tissue retention spring methods now present in the prior art, the present invention provides an improved viscerotomy closure device and method of use, and overcomes the above-mentioned disadvantages and drawbacks of the prior art. As such, the general purpose of the present invention, which will be described subsequently in greater detail, is to provide a new and improved viscerotomy closure device and method of use which has all the advantages of the prior art mentioned heretofore and many novel features that result in a viscerotomy closure device and method of use which is not anticipated, rendered obvious, suggested, or even implied by the prior art, either alone or in any combination thereof.

To attain this, the present invention essentially comprises a loop of suture positioned on a circular stapling device so that when the stapling device is fired and a defect created the loop becomes entrapped in such a way as to become a purse-string around the defect. The invention may include a mesh with a hole in its center and a loop of suture having a knot attached to the mesh.

There has thus been outlined, rather broadly, the more important features of the invention in order that the detailed description thereof that follows may be better understood and in order that the present contribution to the art may be better appreciated.

The invention may also include the mesh and the loop of suture being made from an absorbable suture material. The mesh and the loop of suture may be made from a non-absorbable suture material. The knot may be a Roeder knot. There may be a knot pusher connected to the loop of suture. There may be an end-to-end anastomosis stapler having a staple carrying member with a plurality of staple receiving slots enclosing a plurality of staples and a protruding rod having opposing ends with one end inserted into the staple carrying member. The opposing end of the protruding rod opposite the staple carrying member may be inserted through the mesh hole so that the mesh covers at least a portion of the staple receiving holes. There may be an anvil with its base removably attached to the opposing end of the protruding rod opposite the staple carrying member. There may be an augur-shaped blade attached to the anvil's exterior and extending from its tip to its base. There may be a notch in the anvil's base. The anvil may be generally conical in shape. There may be a plurality of staple clinching grooves in the anvil's base. There are, of course, additional features of the invention that will be described hereinafter and which will form the subject matter of the claims attached.

Numerous objects, features, and advantages of the present invention will be readily apparent to those of ordinary skill in the art upon a reading of the following detailed description of presently current, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved viscerotomy closure device and method of use that has all of the advantages of the prior art circular stapler tissue retention spring methods and none of the disadvantages.

It is another object of the present invention to provide a new and improved viscerotomy closure device and method of use that may be easily and efficiently manufactured and marketed.

An even further object of the present invention is to provide a new and improved viscerotomy closure device and method of use that has a low cost of manufacture with regard to both materials and labor, and which accordingly is then susceptible of low prices of sale to the consuming public, thereby making such viscerotomy closure device and method of use economically available to the buying public.

Still another object of the present invention is to provide a new viscerotomy closure device and method of use that provides in the apparatuses and methods of the prior art some of the advantages thereof, while simultaneously overcoming some of the disadvantages normally associated therewith.

Even still another object of the present invention is to provide a viscerotomy closure device and method of use for closing a hole in a bodily organ, such as one created during a natural orifice transgastric surgery procedure. This allows a loop of suture to be trapped circumferentially by a plurality of staples or metal clips deployed in a circular orientation fired from a circular stapler.

Still yet another object of the present invention is to provide a viscerotomy closure device and method of use for closing a hole in a bodily organ, such as one created during a natural orifice transgastric surgery procedure. This makes it possible to close a viscerotomy.

An additional object of the present invention is to provide a viscerotomy closure device and method of use for closing a hole in a bodily organ, such as one created during a natural orifice transgastric surgery procedure. This enables the wall of a viscus to self-load into a circular stapler.

A further object of the present invention is to provide a viscerotomy closure device and method of use for closing a hole in a bodily organ, such as one created during a natural orifice transgastric surgery procedure. This causes the defect created by stretching the tissue by rotating the augur-shaped blade with the end-to-end anastomosis stapler to be less than the inner diameter of the staple lines.

Lastly, it is an object of the present invention to provide a new and improved viscerotomy closure device and method of use for closing a hole in a bodily organ, such as one created during a natural orifice transgastric surgery procedure.

These together with other objects of the invention, along with the various features of novelty that characterize the invention, are pointed out with particularity in the claims annexed to and forming a part of this disclosure. For a better understanding of the invention, its operating advantages, and the specific objects attained by its uses, reference should be had to the accompanying drawings and descriptive matter in which there is illustrated current embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE CURRENT EMBODIMENT

Figure 1:
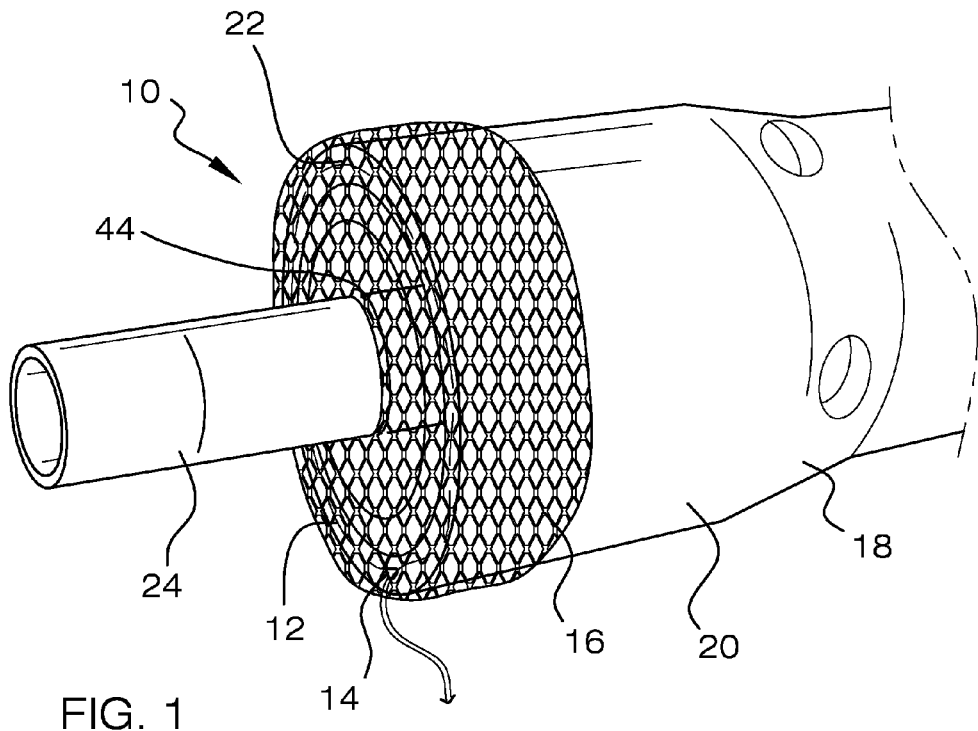
FIG. 1 is a side perspective view of the current embodiment of the viscerotomy closure device and method of use constructed in accordance with the principles of the present invention.

Referring now to the drawings, and particularly to FIGS. 1-8, a current embodiment of the viscerotomy closure device and method of use of the present invention is shown and generally designated by the reference numeral 10.

In FIG. 1, a new and improved viscerotomy closure device and method of use 10 of the present invention for closing a hole in a bodily organ, such as one created during a natural orifice transgastric surgery procedure is illustrated and will be described. More particularly, the viscerotomy closure device and method of use 10 has a loop of suture 12 with a Roeder knot 14 attached to a circular mesh 16. The loop of suture 12 may be attached to the mesh 16 by weaving it through or suturing it into the mesh 16. The mesh 16 has a hole 44 in its center. In the current embodiment, the loop of suture 12 and mesh 16 have a rod 24 inserted through their centers so they can be placed on the end of the staple carrying member 20 of an end-to-end anastomosis stapler 18. Alternatively, the loop of suture 12 and mesh 16 can be placed on the anvil 28 (shown in FIGS. 3-5) of the end-to-end anastomosis stapler 18. In addition, multiple instances of the loop of suture 12 and mesh 16 can be used so that a loop of suture 12 and mesh 16 is on both the staple carrying member 20 and the anvil 28. The loop of suture 12 is connected to a knot pusher 42, which will be described in more detail in the discussion of FIG. 7. The staple carrying member 20 has staple receiving slots 22 in the end covered by the loop of suture 12 and mesh 16. In the current embodiment, loop of suture 12 and mesh 16 are made of polyglactin 910, an absorbable suture material.

Figure 2:
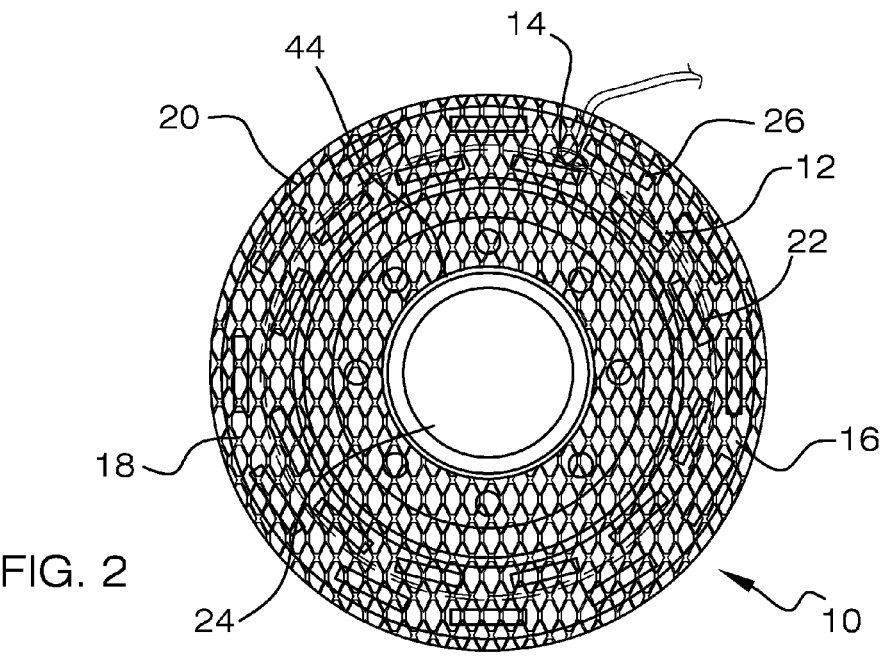
FIG. 2 is a top perspective view of the viscerotomy closure device and method of use of the present invention.

Moving on to FIG. 2, a new and improved viscerotomy closure device and method of use 10 of the present invention for closing a hole in a bodily organ, such as one created during a natural orifice transgastric surgery procedure is illustrated and will be described. More particularly, the viscerotomy closure device and method of use 10 has a loop of suture 12 with a Roeder knot 14 woven through a mesh 16. The loop of suture 12 and mesh 16 are placed over the staple receiving slots 22 of the staple carrying member 20 of an end-to-end anastomosis stapler 18. Rod 24 protrudes through the hole 44 in the center of mesh 16. Staples 26 are visible within staple receiving slots 22. Staples 26 are non-absorbable titanium staples in the current invention, but absorbable staples could also be used.

Figure 3:
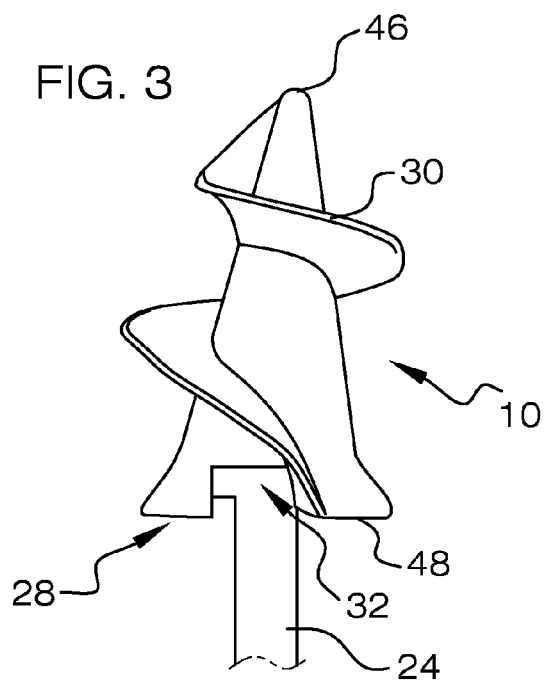
FIG. 3 is a side view of the viscerotomy closure device and method of use of the present invention.

Continuing with FIG. 3, a new and improved viscerotomy closure device and method of use 10 of the present invention for closing a hole in a bodily organ, such as one created during a natural orifice transgastric surgery procedure is illustrated and will be described. More particularly, the viscerotomy closure device and method of use 10 has an anvil 28 with one end attached to the end of rod 24. Anvil 28 is generally conical in shape and has an augur-shaped blade 30 that starts at its tip 46 and twists around to end at its base 48 below the level of the anvil 28. Blade 30 directs any tissue 38 it comes into contact with downward, causing the tissue 38 to become engaged between the staple carrying member 20 and the anvil 28 simply by pushing the anvil 28 against the tissue 38 and rotating the end-to-end anastomosis stapler 18 about its axis. The base 48 of anvil 28 has a notch 32 so the final twist of the blade 30 enables the stretched tissue 38 defect it creates to not be greater than the inner diameter of the staple line defined by the staple receiving slots 22. Additionally, a conical spacer can be used below the anvil 28 to ensure that when the end-to-end anastomosis stapler 18 is fired, the staples 26 engage with the entire circumference of the tissue 38.

Figure 4:
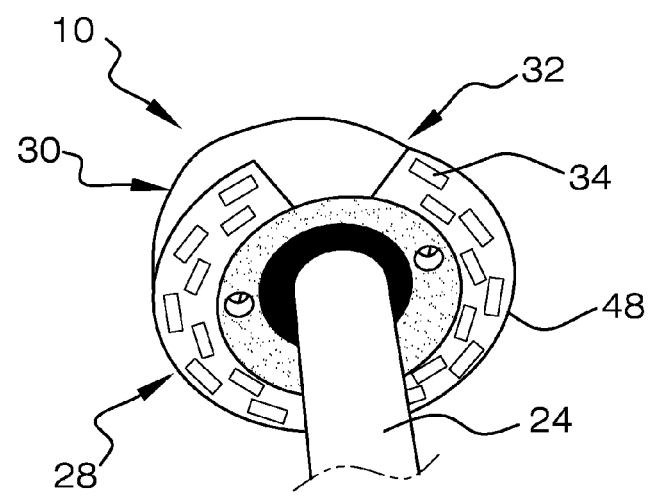
FIG. 4 is a bottom perspective view of the viscerotomy closure device and method of use of the present invention.

In FIG. 4, a new and improved viscerotomy closure device and method of use 10 of the present invention for closing a hole in a bodily organ, such as one created during a natural orifice transgastric surgery procedure is illustrated and will be described. More particularly, the viscerotomy closure device and method of use 10 has an anvil 28 with staple clinching grooves 34 in its base 48. Staple clinching grooves 34 are aligned with staple receiving slots 22 so that the ends of staples 26 are clinched by staple clinching grooves 34 when the end-to-end anastomosis stapler 18 is fired.

Figure 5:
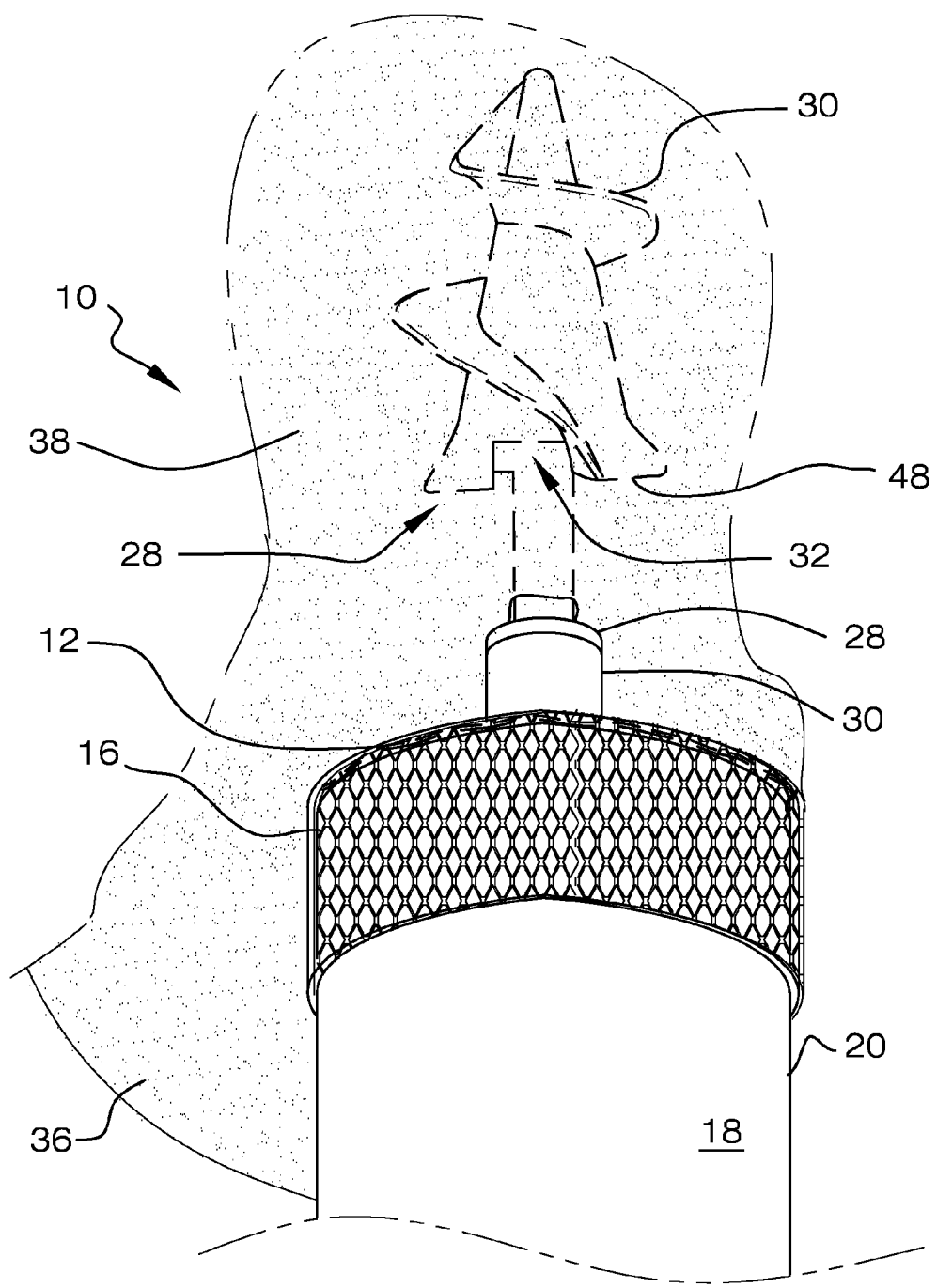
FIG. 5 is a side perspective view of the viscerotomy closure device and method of use of the present invention.

Furthermore, in FIG. 5, a new and improved viscerotomy closure device and method of use 10 of the present invention for closing a hole in a bodily organ, such as one created during a natural orifice transgastric surgery procedure is illustrated and will be described. More particularly, the viscerotomy closure device and method of use 10 is depicted in use with blade 30 of anvil 28 in contact with the tissue 38 of an organ 36. As the blade is rotated 180°, the tissue 38 self-loads into the space between the anvil 28 and staple carrying member 20 because of the augur-shaped blade 30.

Figure 6:
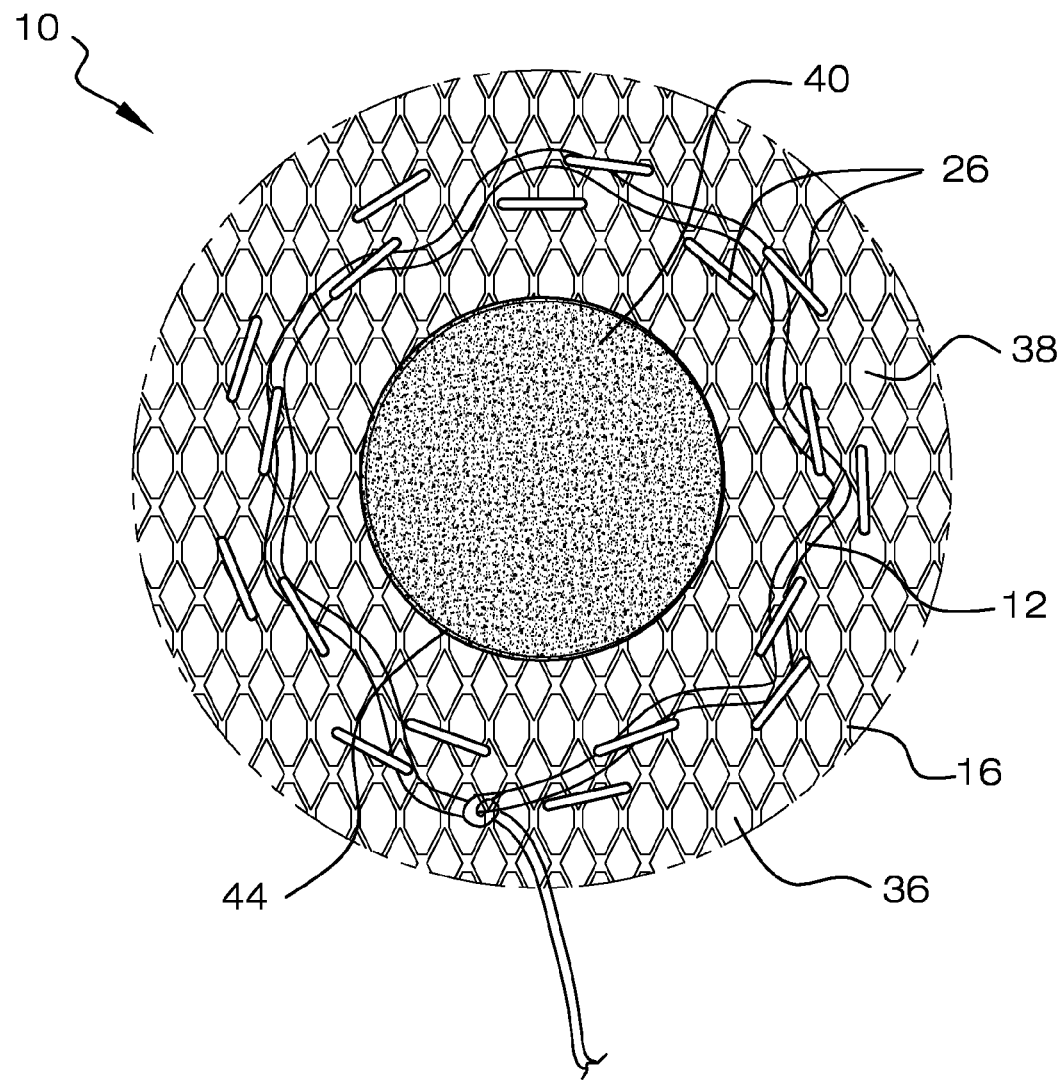
FIG. 6 is a top perspective view of the viscerotomy closure device and method of use of the present invention.

In FIG. 6, a new and improved viscerotomy closure device and method of use 10 of the present invention for closing a hole in a bodily organ, such as one created during a natural orifice transgastric surgery procedure is illustrated and will be described. More particularly, the viscerotomy closure device and method of use 10 is depicted in use subsequent to the firing of end-to-end anastomosis stapler 18. The end-to-end anastomosis stapler 18 has created a viscerotomy 40 in tissue 38 of organ 36 and circumferentially secured the loop of suture 12 and mesh 16 at the margins of the viscerotomy 40 with staples 26. The end-to-end anastomosis stapler 18 has also cut the center of mesh 16 so the hole 44 in the center of mesh 16 is aligned with the outer edge of the viscerotomy 40.

Figure 7:
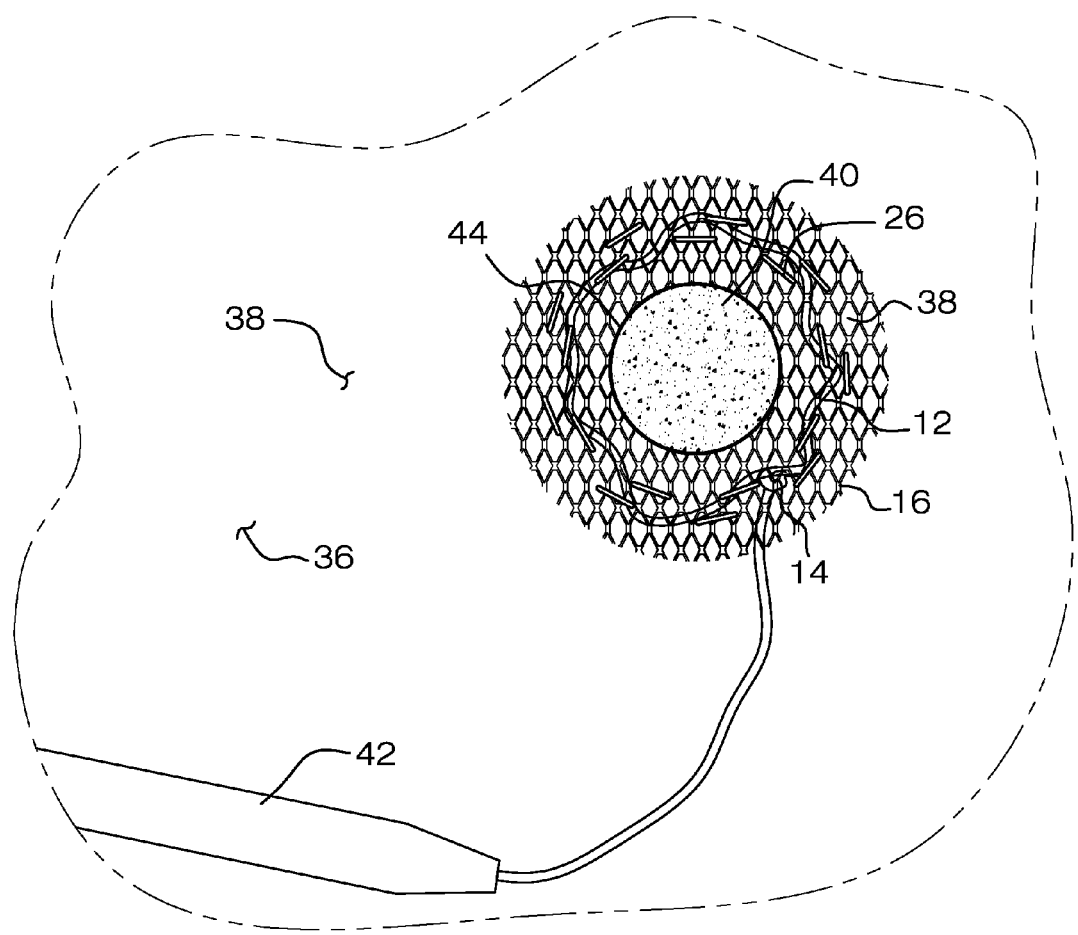
FIG. 7 is a top perspective view of the viscerotomy closure device and method of use of the present invention.

Moving on to FIG. 7, a new and improved viscerotomy closure device and method of use 10 of the present invention for closing a hole in a bodily organ, such as one created during a natural orifice transgastric surgery procedure is illustrated and will be described. More particularly, the viscerotomy closure device and method of use 10 is shown in use subsequent to the tiring of end-to-end anastomosis stapler 18. Staples 26 secure mesh 16 and loop of suture 12 around the exterior of viscerotomy 40. Knot pusher 42 is used to cinch down the loop of suture 12, thereby tightly closing the viscerotomy 40. The Roeder knot 14 is then tightened to maintain the cinch in the current embodiment. Alternatively, extracorporeal knots can be placed using the knot pusher 42, or some other locking device can be employed.

Figure 8:
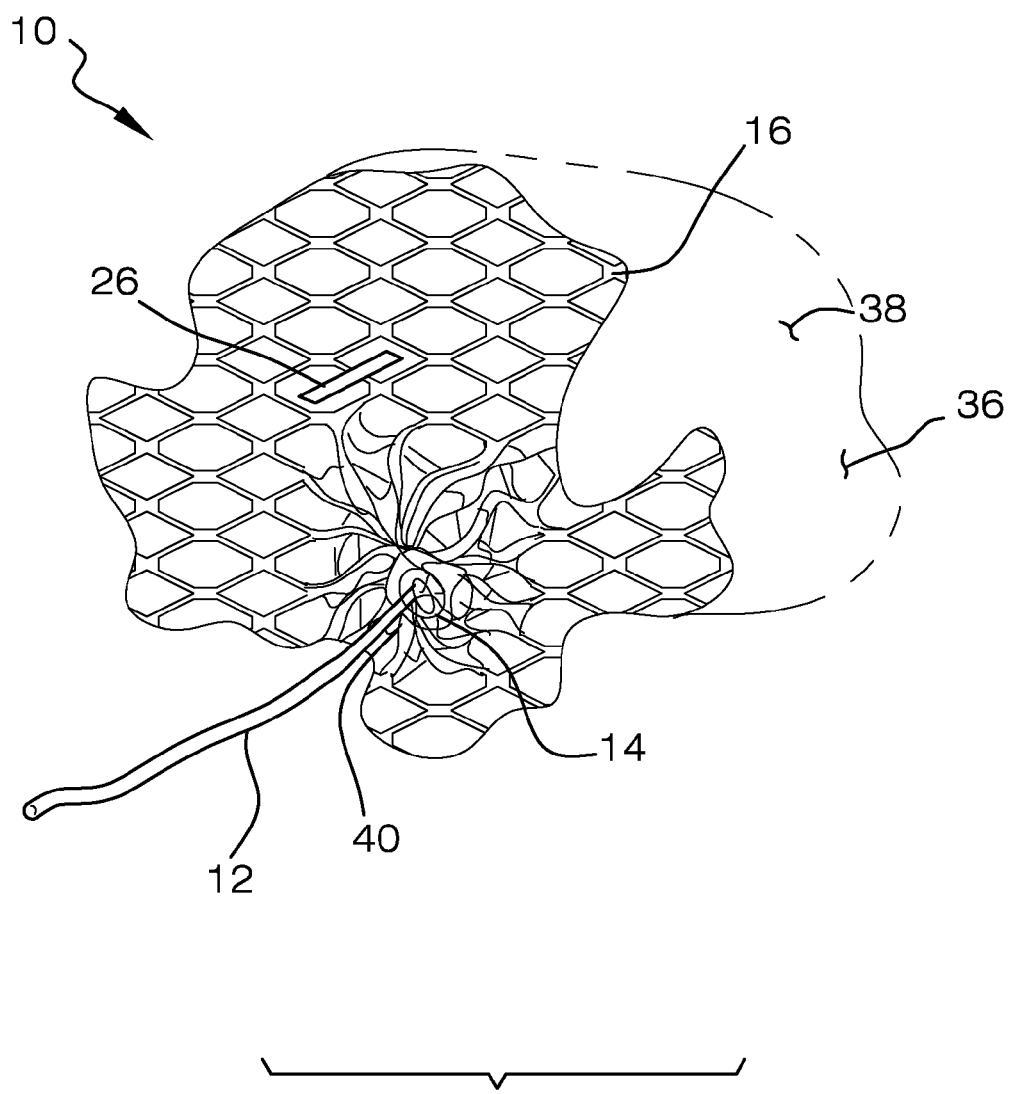
FIG. 8 is a top perspective view of the viscerotomy closure device and method of use of the present invention. The same reference numerals refer to the same parts throughout the various figures.

Concluding with FIG. 8, a new and improved viscerotomy closure device and method of use 10 of the present invention for closing a hole in a bodily organ, such as one created during a natural orifice transgastric surgery procedure is illustrated and will be described. More particularly, the viscerotomy closure device and method of use 10 is depicted in use with the loop of suture 12 cinched down and secured by the Roeder knot 14. The portion of loop of suture 12 connected to the knot pusher 42 has been cut off, and the knot pusher 42 has been removed. The cinched loop of suture 12 has tightly closed the viscerotomy 14 in tissue 38 of organ 36.

In use, it can now be understood that a loop of suture with a Roeder knot and a connected knot pusher is attached to a mesh with a hole in its center. The protruding rod of an end-to-end anastomosis stapler is inserted through the hole in the mesh's center so that the mesh and loop of suture cover the staple receiving slots of the end-to-end anastomosis stapler's staple carrying member. The base of an anvil is then attached to the end of the protruding rod. A viscerotomy is created by passing a hollow needle through a patient's skin into a patient's bodily organ. One end of a wire is advanced through the hollow needle into the bodily organ. This end of the wire is then pulled through the patient's mouth and attached to the tip of the anvil. The tip of the anvil is brought into contact with tissue by pulling on the other end of the wire. The augur-shaped blade mounted on the anvil is rotated by the end-to-end anastomosis stapler, which feeds the tissue into the space between the anvil and the staple carrying member. Use of the hollow needle and wire ensures there is a safe point on the bodily organ to pass the anvil through and maintains the tissue in tension against the augur-shaped blade while the anvil is rotated by the end-to-end anastomosis stapler. When the tissue is in position, the end-to-end anastomosis stapler is fired. The staples are ejected from the staple receiving slots in the staple carrying member and pass through the mesh and the tissue prior to having their ends clinched by staple clinching grooves in the anvil's base. The stapled mesh secures the loop of suture to the tissue around the resulting viscerotomy. The end-to-end anastomosis stapler and the wire are then removed from the patient. The knot pusher is used to cinch down the loop of suture and tighten the Roeder knot to tightly close the viscerotomy. The portion of the loop of suture connected to the knot pusher is then severed from the portion of the loop of suture connected to the mesh, and the knot pusher and the severed portion of the loop of suture are removed.

While a current embodiment of the viscerotomy closure device and method of use has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable absorbable or non-absorbable suture material may be used instead of the polyglactin 910 described. Also, the non-absorbable titanium staples may be replaced by absorbable staples. Furthermore, the orientation of the circular staples could be changed to make them deploy perpendicularly to the route of the loop of suture, or the loop of suture could be placed in a zigzag pattern over the staple receiving slots so the loop of suture will be entrapped by the staples, thereby eliminating the use of mesh. And although closing a hole in a bodily organ, such as one created during a natural orifice transgastric surgery procedure has been described, it should be appreciated that the viscerotomy closure device and method of use herein described is also suitable for closing a gastrotomy or defect to any hollow viscus, e.g. colon, vagina, or intestine. Furthermore, a wide variety of locking devices, such as a clip, may be used instead of the Roeder knot described.

Therefore, the foregoing is considered as illustrative only of the principles of the invention. Further, since numerous modifications amid changes will readily occur to those skilled in the art, it is not desired to limit the invention to the exact construction and operation shown and described, and accordingly, all suitable modifications and equivalents may be resorted to, falling within the scope of the invention.

I claim:

1. A viscerotomy closure device comprising:
a mesh having a center;
a mesh hole, wherein said center of said mesh defines said mesh hole; and
a loop of suture having a knot, wherein said loop of suture is attached to said mesh;
an end-to-end anastomosis stapler having a staple carrying member, a plurality of staple receiving slots defined by said staple carrying member, a plurality of staples enclosed by said staple receiving slots, and a protruding rod having opposing ends with one end inserted into said staple carrying member, wherein said opposing end of said protruding rod opposite said staple carrying member is inserted through said mesh hole so that said mesh covers at least a portion of said staple receiving holes; an anvil having a tip, a base, and an exterior, wherein said base is removably attached to said opposing end of said protruding rod opposite said staple carrying member; and an augur-shaped blade attached to said exterior of said anvil and extending from said tip to said base.

2. The viscerotomy closure device of claim 1, wherein said mesh and said loop of suture are made from an absorbable suture material.

3. The viscerotomy closure device of claim 1, wherein said mesh and said loop of suture are made from a non-absorbable suture material.

4. The viscerotomy closure device of claim 1, wherein said knot is a Roeder knot.

5. The viscerotomy closure device of claim 1, further comprising a knot pusher connected to said loop of suture.

6. The viscerotomy closure device of claim 1, further comprising a notch defined by said base of said anvil.

7. The viscerotomy closure device of claim 1, wherein said anvil is generally conical in shape.

8. The viscerotomy closure device of claim 1, further comprising a plurality of staple clinching grooves, wherein a plurality of grooves in said base of said anvil define said staple clinching grooves.

9. A viscerotomy closure device comprising:
An end-to-end anastomosis stapler having a staple carrying member, a plurality of staple receiving slots defined by said staple carrying member, a plurality of staples enclosed by said staple receiving slots, and a protruding rod having opposing ends with one end inserted into said staple carrying member;
a mesh having a center hole, wherein said opposing end of said protruding rod opposite said staple carrying member is inserted through said center hole in said mesh such that said mesh covers at least a portion of said staple receiving holes;
a loop of suture having a knot, wherein said loop of suture is attached to said mesh so that said plurality of staples can staple said loop of suture to tissue;
an anvil having a tip, a base, and an exterior, wherein said base is removably attached to said opposing end of said protruding rod opposite said staple carrying member; and an augur-shaped blade attached to said exterior of said anvil and extending from said tip to said base.

10. The viscerotomy closure device of claim 9, further comprising a notch defined by said base of said anvil.

11. The viscerotomy closure device of claim 10, further comprising a plurality of staple clinching grooves, wherein a plurality of grooves in said base of said anvil define said staple clinching grooves.

12. The viscerotomy closure device of claim 11, further comprising a knot pusher connected to said loop of suture.

13. The viscerotomy closure device of claim 9, wherein said loop of suture is attached to said mesh by being woven through said mesh.

* * * * *